United States Patent
Braun et al.

(10) Patent No.: US 6,819,843 B1
(45) Date of Patent: Nov. 16, 2004

(54) DEVICE AND METHOD FOR PHOTOLITHOGRAPHICALLY IRRADIATING BIOLOGICAL SUBSTANCES

(75) Inventors: Aron Braun, Berlin (DE); Arno Heuermann, Berlin (DE)

(73) Assignee: Epigenomics AG, Berlin (DE)

( * ) Notice: Subject to any disclaimer, the term of this patent is extended or adjusted under 35 U.S.C. 154(b) by 0 days.

(21) Appl. No.: 09/980,194

(22) PCT Filed: May 12, 2000

(86) PCT No.: PCT/DE00/01540
§ 371 (c)(1),
(2), (4) Date: Jul. 23, 2002

(87) PCT Pub. No.: WO00/69553
PCT Pub. Date: Nov. 23, 2000

(30) Foreign Application Priority Data

May 14, 1999 (DE) .......................... 199 22 941

(51) Int. Cl.⁷ .............................................. G02B 6/04
(52) U.S. Cl. ................. 385/115; 606/2; 606/3; 606/10; 606/11; 606/12; 606/13; 606/14; 606/15; 606/16
(58) Field of Search .................. 385/115; 606/2, 606/3, 10–16

(56) References Cited

U.S. PATENT DOCUMENTS

| | | | | |
|---|---|---|---|---|
| 3,689,932 A | * | 9/1972 | Heinz | 346/29 |
| 4,407,964 A | * | 10/1983 | Elings et al. | 436/518 |
| 5,302,999 A | * | 4/1994 | Oshida et al. | 355/1 |
| 5,501,680 A | * | 3/1996 | Kurtz et al. | 606/9 |
| 5,729,331 A | * | 3/1998 | Tanaka et al. | 355/53 |
| 5,908,415 A | * | 6/1999 | Sinofsky | 606/7 |
| 5,968,036 A | * | 10/1999 | Goodman et al. | 606/12 |
| 6,002,466 A | | 12/1999 | Brauch et al. | 355/53 |
| 6,156,494 A | | 12/2000 | Adams et al. | 435/4 |

* cited by examiner

Primary Examiner—Brian Healy
Assistant Examiner—Daniel Petkovsek
(74) Attorney, Agent, or Firm—Kriegsman & Kriegsman

(57) ABSTRACT

A device and a method for the photolithographic exposure of biological substances is described, which comprises at least one light source, a bundle of optical fibers and a control unit, whereby each of the optical fibers can be controlled by light independently from one another and/or light can be coupled to each fiber independently.

The device is particularly suitable for the exposure of DNA, PNA or peptide chips.

19 Claims, 2 Drawing Sheets

DEVICE AND METHOD FOR PHOTOLITHOGRAPHICALLY IRRADIATING BIOLOGICAL SUBSTANCES

BACKGROUND OF THE INVENTION

The invention concerns a device and a method for the photolithographic exposure of biological substances.

DNA chips are ultra-small, generally planar surfaces, on which a large number of different oligomers (short, single-stranded DNA molecules) are introduced in a spatially organized manner. Such chips are used, for example, for the parallel recognition of numerous DNA sequences in a prepared tissue specimen. For this purpose, the chip surface is wetted with a solution of single-stranded DNA segments from the tissue specimen. Complementary DNA segments from the solution are deposited on the corresponding oligomers introduced on the chip surface (hybridization). After this, a determination is made of which places on the chip a hybridization has occurred by means of suitable methods, such as, e.g., fluorescent labeling. If one knows where on the chip the respective oligomers are introduced, conclusions can be made relative to the DNA sequences in the tissue specimen. For this purpose, usually a dense rectangular grid is defined on the chip support surface. One type of oligomer is introduced at each grid point in the form of a small spot. The maximum possible number of different DNA sequences on the chip is consequently equal to the number of grid points. Since one wishes to introduce as many types of oligomers as possible on one chip, but the chips must be as small as possible at the same time in order to be able to effectively hybridize, it is an important objective in the production of DNA chips to achieve as high a grid density as possible.

Different methods for DNA chip production are known in the prior art:

1) All oligomers are synthesized individually in a conventional manner in the test tube and then are pipetted onto the provided grid points on the support, typically by an automatic micropipetting device. This method is very time-consuming and expensive, since each oligomer must be prepared or purchased individually and must be introduced by hand into the pipetting device. The grid density is limited by the high angular imprecision of the typical piezoelectric micropipettes that are presently available.

2) The oligomers are synthesized directly on the chip by means of an automatic pipetting device. The oligomer chain provided on each grid point is built up base by base (nucleobases). The chemical method is basically the same as in conventional oligomer synthesis in the test tube. The difference is that all oligomers are produced simultaneously directly at the provided determination site by a single automatic device. The separate operating steps of oligomer synthesis and micropipetting of method 1) are thus combined into one uniform operating step. This in-situ synthesis normally proceeds as follows: The automatic pipetting device sequentially drops the first nucleobase provided for each grid point onto a prepared substrate. This is mechanically not very time-consuming or expensive, since there are only 4 different nucleobases (C, T, G, A). For example, 4 micropipettes coupled to one another can be used for this purpose. After applying the first nucleoside building block at each grid point, the substrate is washed and after a "capping step", the protecting groups at the 5'—OH functions are removed, in order to make possible the reaction with the respective subsequent nucleoside building block. After this, the second nucleobase is pipetted onto each grid point. The substrate is then washed again and deprotected. In this way, the necessary oligomer chains are constructed step by step on each grid point. This method is not particularly rapid, since each nucleobase must be newly pipetted one after the other onto each grid point. As in the case of method 1), the grid density is limited by the imprecision of the micropipettes. The imprecision is even worse here, since each grid point must be contacted several times sequentially in a way that is as identical as possible.

3) The oligomers are synthesized directly on the support as in 2), but the targeted binding of the correct nucleobases to the correct grid points is done by means of a completely parallel, photolithographic technique instead of sequential, target-precise pipetting steps. The method is based on the fact that the 5'—OH protecting groups of oligonucleotides can be removed in a targeted manner by light of a specific wavelength. By suitable local irradiation patterns, oligonucleotide ends can thus be made capable of reaction at precisely those grid points at which one wishes to introduce a new nucleoside in the next step. By complete wetting of the chip surface with a nucleotide building-block solution, a nucleotide base is thus bound only to the sites that have been previously exposed, and all unexposed sites remain unchanged. The local exposure patterns are produced by positioning a photomicrographic black-white mask between the substrate and the light source. The mask covers all of the grid points, which are not to be made capable of reaction. The elongation of the oligomer chains by one nucleobase at all grid points is then conducted as follows: Those grid points which must be extended by the first of the 4 possible types of nucleobases (e.g., C) are precisely exposed by means of a first mask. Then the chip is wetted with a solution of the corresponding nucleotide base, whereupon only the exposed points are elongated by this base. Since the newly bound bases all have a protecting group, they do not further react in the following steps until their protecting groups are cleaved by another exposure. The chip is washed after this reaction step. Now, those grid sites, which must be elongated by the second of the 4 possible types of nucleobases (e.g., T) are precisely exposed by means of a second mask. Then the chip is again wetted with a solution of the corresponding nucleotide building block and the exposed sites in this way are elongated by this base. The procedure is the same for the remaining two bases (e.g., G and A). For the elongation of all oligomers by one nucleobase, one consequently requires four exposure steps and 4 photomasks. This method is very efficient due to the high parallel operation, and it is also suitable for obtaining very high grid densities, due to the high precision that can be obtained with photolithography. Of course, the method is very time-consuming and thus expensive, since a large number of photomasks must first be created for the production of a specific type of chip. Also, rigid requirements are placed on the positioning accuracy of the masks during exposure in the case of high grid densities, and these requirements can be fulfilled efficiently only by using very expensive apparatus.

4) The same method is applied as in 3), but instead of the large number of photographic masks, only a single, transmissive, liquid crystal display, which is controlled electronically and serves as a dynamic mask, is used. This method is simple and inexpensive, since photographic masks need not be produced and there is thus no positioning problem. One possible problem of this method is the limited optical contrast of the liquid crystal displays that are currently available (maximum 1:100). The light intensity ratio between exposed and covered points is thus reduced, which can have as a consequence a reduction in yield in the case of oligomer synthesis.

These methods of the prior art have a number of disadvantages. Of the above-described production methods for DNA chips, the photolithographic method with dynamic liquid crystal masks is the only one that permits a simple, inexpensive and reliable production of chips with high grid density. The deficient contrast of liquid crystal displays, however, has as a consequence a reduction in the quality of the oligomer points, which in the final analysis reduces the detection sensitivity of the chip.

SUMMARY OF THE INVENTION

The object of the present invention is thus to create a device, which overcomes the disadvantages of the prior art. Another object of the invention is the creation of another method for the photolithographic exposure of biological substances.

The object is solved by the characterizing features of the main claim. Advantageous embodiments of the invention are characterized in the dependent subclaims.

The object is solved according to the invention in that a device for the photolithographic exposure of biological substances is created, comprising at least one light source, a bundle of light-guiding optical fibers and a control unit, whereby each of the optical fibers can be controlled by light and/or light can be coupled to these fibers, independently of one another.

It is preferred that the light source emits monochromatic or continuous light in a wavelength range of 100 to 800 nm. It is particularly preferred that the light source is a laser, a luminous diode, a metal-vapor lamp, a gas-discharge lamp, a gas-excitation lamp, an incandescent-filament lamp or an arc lamp.

It is further advantageous that luminous diodes and/or optical switches are arranged for controlling the individual optical fibers.

It is particularly advantageous that the substances to be exposed are introduced directly at the ends of the optical fibers. However, it is also preferred that substances to be exposed are arranged on a separate support.

It is most especially preferred that substances to be exposed are arranged on a separate support, and that this support is a DNA chip, a PNA chip or a peptide chip.

According to the invention, the device preferably also has at least one detector.

It is thus preferred that at least one of the detectors is arranged in such a way that the latter detects the light used for exposure and/or at least one detector is arranged in such a way that it detects light reflected from the exposed substances and/or produced by fluorescence and that optical fibers and/or bundles of optical fibers are optionally provided for conducting light for the detectors. It is particularly preferred that the detectors are CCD detectors and/or CCD cameras.

It is very particularly preferred that a dynamic mask is provided for controlling the individual optical fibers. It is also particularly preferred that a set of static masks is provided for controlling the individual optical fibers.

A device according to the invention is most preferred, wherein the light source emits a spectrum of wavelengths that can effect the deprotection of nucleotides, nucleotide analogs and peptide nucleic acid building blocks for chain elongation and for constructing oligomers, and that a bundle of optical fibers is arranged between this light source and the substrate, in which light can be coupled selectively by targeted control, and that the solid phase on which the oligomer synthesis occurs is positioned precisely and rigidly behind the bundle of optical fibers, and that the solid phase on which the oligomer synthesis occurs is arranged in a chamber in which the solutions and/or reagents necessary for DNA or PNA synthesis can be introduced to this solid phase by additional devices.

It is preferred according to the invention that a separate support is arranged as the solid phase on which the oligomer synthesis occurs. It is further preferred according to the invention that the ends of the optical fibers themselves are the solid phase for conducting the oligomer synthesis.

Another subject of the present invention is a method for the photolithographic exposure of biological substances, wherein these substances are arranged on a surface or at the end of an optical fiber and exposed by means of light, which is guided by the optical fiber and originates from a light source, which is arranged at the other end of the optical fiber, whereby each point which lies opposite one end of the optical fiber is exposed independently of the other points, whereby the exposure pattern is selected in advance by means of a control unit.

It is specifically preferred, for exposure of DNA or PNA chips, that light of wavelengths which cause the deprotection of nucleotides, nucleotide analogs and peptide nucleic acid building blocks for chain elongation and for construction of oligomers be used, and that a bundle of optical fibers is arranged between this light source and the substrate, in which [fibers], light is selectively coupled to each fiber by targeted control, and that the solid phase on which oligomer synthesis occurs is positioned precisely and rigidly behind the bundle of optical fibers, and that the solid phase on which the oligomer synthesis occurs is arranged in a chamber in which solutions and/or reagents that are necessary for DNA or PNA synthesis are introduced onto the solid phase by additional devices.

It is further preferred according to the invention that subsequent hybridizations are conducted with a target DNA after the oligomerization has been produced on the DNA or PNA chips.

Another subject of the invention is a method, wherein one uses a device according to the invention for conducting the method.

It has been found surprisingly that the device according to the invention makes possible a simple and moderately priced photolithographic production of DNA chips of high grid density with an exposure contrast of far greater than 1:100. In this way, the simple production of qualitatively superior DNA chips in any laboratory is made possible for the first time.

The device according to the invention and the method solve the object that was set forth in a completely novel manner by combination of commercially available components. It makes possible the inexpensive production of DNA chips in a quality that has not been previously possible.

The basic concept of the device and of the method according to the invention consists of the fact that a specific exposure pattern is produced on the substrate not by targeted masking of grid points by means of a static or dynamic mass, but rather light is introduced directly by means of an optical fiber light guide individually to each of the grid points to be exposed. Therefore, the end of an optical fiber must be introduced over each grid point such that when light is coupled to the fiber, the light exiting at the end precisely illuminates the corresponding grid point. Consequently, the number of optical fibers that are necessary corresponds precisely to the grid points that are provided. In order to be able to produce any desirable exposure pattern, an independent control of each individual optical fiber must be made of whether or not light is coupled to it at a given time point. By coupling or not coupling light in a targeted manner to the correct fibers, those grid points that must be activated can be exposed exclusively at each exposure step, while all others remain unexposed.

The targeted coupling of light into the correct fibers each time must be controlled in a fully automatic electronic manner, and thus the method can be conducted in a simple way. One possible technical solution is to introduce a light source that can be turned on and off at the beginning of each optical fiber, which belongs to just this one fiber (e.g., a laser diode of the correct wavelength). Another possibility is the use of commercially available optical switches that can be controlled electrically. These involve a hardware component with 2 terminals or 2 optical fibers and an electrical control input. It can be determined by an electrical signal at the control input whether or not the two optical fibers will be optically combined. One optical switch and two optical fibers are thus necessary for each grid point. Light is permanently coupled to the free end of the first fiber, while the free end of the second fiber serves as the light output and is attached over the respective grid point. A single light source is sufficient for light coupling, if all input fibers are bundled correspondingly.

Both methods of targeted light coupling are equivalent for the electrical control. Only one control electronics unit is required, which can individually address each grid point. Basically, it does not matter whether light diodes or optical switches are controlled.

Another possibility for the targeted light coupling in the individual fibers of the optical fiber bundle is the use of automatically positioned static masks (e.g., photomasks or shadow masks) or an electronically controllable dynamic mask (e.g., an LCD), which is introduced between the light source and the input side of the fiber bundle. Any fiber inputs into which light will not be coupled at the respective exposure step can be masked in a targeted manner with the masks. The masks can be arranged geometrically in a different manner and particularly may be much larger than the array surface to be exposed, since the bundle of optical fibers can be fanned out or can be separated into individual fibers on the coupling side, as desired.

For the maximally attainable grid density of the chip, it does not matter how much space the light coupling system (individual light sources, optical switches, static or dynamic masks) requires. The grid density is only dependent on how densely the fiber ends on which the light emerges can be bundled. This possibility of geometrical packing represents the most essential advantage of the invention. In the case of a typical fiber diameter of approximately 100 micrometers, approximately 1000 grid points can be obtained per square centimeter on the exposure side, which is sufficient for many applications.

If it is too time-consuming to arrange the ends of the optical fibers that are to be introduced over the substrate in a uniform, rectangular lattice grid, one may also attach an unarranged fiber bundle over the substrate. The points on a chip produced in this way are then no longer grid-shaped, but are arranged randomly and irregularly. Nevertheless, for all chips, which have been produced by the same arrangement of optical fibers, the positions of the points are identical. Basically, one can know which type of oligomer has been synthesized at which position of the chip. It is sufficient for a given synthesis arrangement with a random bundling of light fibers to couple light sequentially to each individual optical fiber a single time and to establish the positions of the emitted light cone with a high-resolving CCD detector, which is placed in the plane of the substrate. A complete table with the assignment of all control addresses to the corresponding x-y substrate positions can be prepared in this way. This information is later used for evaluating all chips that are prepared with the corresponding arrangement.

For an evaluation according to the method of fluorescent labeling, one may optionally use the same unrastered arrangement of optical fibers, which has been used in the production, but in this case light is now not coupled to the other end of the fiber, but rather the fluorescent light occurring now in points on the substrate side is measured by means of photodetectors. For this purpose, a separate photodetector must be introduced at the position of the light source(s) at each fiber end. Such an optical reading system with optical fibers can considerably simplify chip detection in comparison with conventional detection methods by means of CCD detectors.

A very interesting and novel variant of application of the DNA chip synthesis method described here is the synthesis of oligomers directly onto the ends of the optical fibers instead of onto a separate substrate. This can be achieved by chemically preparing the end surfaces of the optical fibers through which the light is emitted in a way similar to the preparation of conventional DNA chip support surfaces. In this way, each end of the optical fiber is itself a small, independent support, on which one type of oligomer can be synthesized precisely with the usual photolithographic chemistry. The photoactivating light is thus no longer irradiated from outside onto the support surface, but is emitted directly at the support surface from the transparent, light-guiding support material. Instead of a single support surface with many different, small oligomer points, one now has a plurality of separate small support surfaces, each with one type of oligomer thereon. As in the case of conventional chips, the oligomer points must lie densely next to one another, and thus they can be used for an efficient hybridization. This can be achieved, as described above, by dense bundling of the fiber ends.

With such a synthesis on the ends of optical fibers, the family of oligomer points that is produced remains inseparably connected to the device used for the production. Hybridization and subsequent detection are then also conducted at the ends of the optical fibers, whereby the optical fibers are again used for a fluorescent detection in the direction opposite to the readout of the fluorescent signals. After one synthesis-hybridization-detection cycle, the tips of the optical fibers can be chemically cleaned and the device can thus be made ready for a new synthesis.

BRIEF DESCRIPTION OF THE DRAWINGS

The present invention will be explained in more detail on the basis of the attached drawing.

Here.

DESCRIPTION OF THE INVENTION

Figure 1:
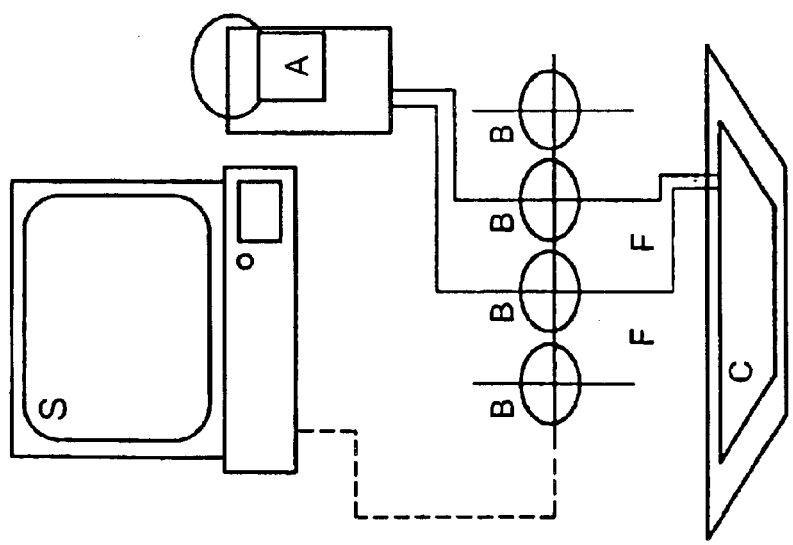
FIG. 1 shows the schematic arrangement of a first embodiment of the device of the invention, in which the fibers are controlled by optical switches.

A first example of embodiment of a device according to the invention is shown in FIG. 1. The light from light source A is guided over the electrically controlled optical switch B onto the array support C by means of optical fiber F. The control S, preferably a computer, provides for the corresponding control of the individual switches B in a pregiven manner in the form of a dynamic or static mask.

Figure 2:
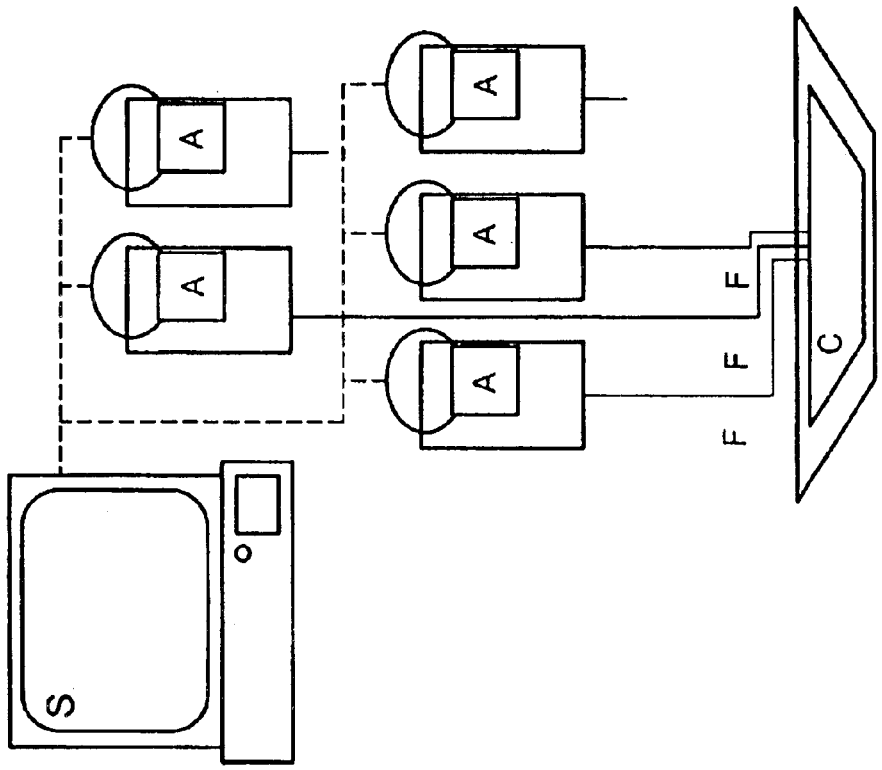
FIG. 2 shows the schematic arrangement of a second embodiment of the device according to the invention, in which the control of the fibers is represented by individual light sources.

A second example of embodiment of a device according to the invention is shown in FIG. 2. The light is guided onto the array support C by means of the optical fiber F from a plurality of light sources A. The control S, preferably a computer, provides for the corresponding control of the individual switches A in a pregiven manner. Here also, the control can be produced in the form of a dynamic or static mask.

Figure 3:
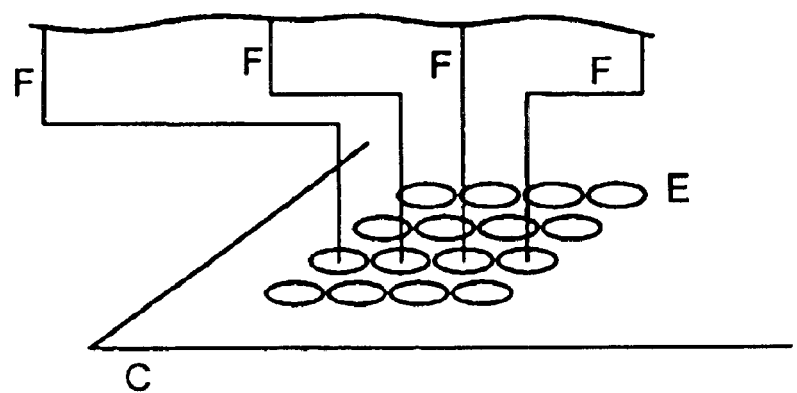
FIG. 3 shows the schematic arrangement during the exposure of a separate support (chip) and FIG. 4 shows the schematic arrangement during exposure, whereby the substrate is found directly at the ends of the fibers.

FIG. 3 shows in detail how the individual substrate points E on the array support C are exposed by optical fibers F.

Figure 4:
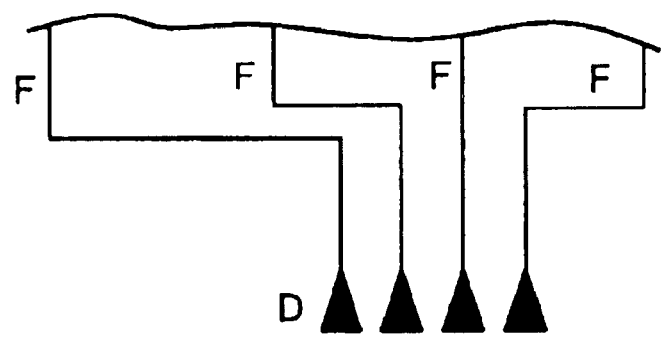

FIG. 4 shows that the substrates are arranged directly at the ends of the optical fibers F.

It is clear to the person of average skill in the art how the individual components are to be arranged in a device according to the invention. Also, the corresponding programming of the control by means of computer programs is known in and of itself to the person of average skill in the art.

List of Reference Symbols

A: light source
B: electrically controlled optical switches
C: array support
D: substrate at the fiber ends
E: substrate points on the array support
F: optical fiber
S: control (computer)

What is claimed is:

1. A device for the synthesis of oligonucleotide arrays by photolithographic exposure of a surface, comprising:
   at least one light source,
   a plurality of light guided optical fibers for the photolithographic exposure of a surface to generate an oligonucleotide array on the surface, and
   a control unit, wherein each of the optical fibers can be controlled independently of one another by light and/or light can be coupled to each of the optical fibers; independently of one another.

2. The device according to claim 1, further characterized in that the light source emits monochromatic or continuous light in a wavelength range of 100 to 800 nm.

3. The device according to claim 2, further characterized in that the light source is a laser, a luminous diode, a metal-vapor lamp, a gas-discharge lamp, a gas-excitation lamp, an incandescent-filament lamp or an arc lamp.

4. The device according to claim 1, further characterized in that luminous diodes and/or optical switches are arranged for the control of the individual optical fibers.

5. The device according to claim 1, further characterized in that the surface to be exposed is introduced directly at the ends of the optical fibers.

6. The device according to claim 1, further characterized in that the surface to be exposed is arranged on a separate support.

7. The device according to claim 1, further characterized in that the surface to be exposed is arranged on a separate support, whereby this support is a DNA chip, a PNA chip or a peptide chip.

8. The device according to claim 1, further characterized in that the device additionally comprises at least one detector.

9. The device according to claim 8, further characterized in that at least one of the detectors is arranged in such a way that it detects the light used for the exposure and/or at least one detector is arranged in such a way that it detects the light reflected from the exposed substances and/or produced by fluorescence and that optical fibers and/or bundles of optical fibers are optionally provided for light guiding for the detectors.

10. The device according to one of claims 8 or 9, further characterized in that the detectors are CCD detectors and/or CCD cameras.

11. The device according to claim 1, further characterized in that a dynamic mask is provided for the control of the individual optical fibers.

12. The device according to claim 1, further characterized in that a set of static masks is provided for the control of the individual optical fibers.

13. The device according to claim 1, further characterized in that the light source emits a spectrum of wavelengths that bring about the deprotecting of nucleotides, nucleotide analogs and peptide nucleic acid building blocks for the elongation of the chain and for the construction of oligomers, and that between this light source and the substrate is arranged a bundle of optical fibers, to which light can be selectively coupled each time by targeted control, and that the solid phase on which the oligomer synthesis occurs is positioned precisely and rigidly behind the bundle of optical fibers, and that the solid phase on which oligomer synthesis occurs is arranged in a chamber in which the solutions and/or reagents necessary for the DNA or PNA synthesis can be introduced onto this solid phase by other devices.

14. The device according to claim 13, further characterized in that a separate support is arranged as the solid phase on which oligomer synthesis occurs.

15. The device according to claim 13, further characterized in that the ends of the optical fibers themselves are the solid phase for conducting the oligomer synthesis.

16. A method for the synthesis of oligonucleotide arrays by photolithographic exposure of a surface, whereby the nucleotides are generated on a surface or at the end of an optical fiber by exposure to light, which is guided by the optical fiber and which originates from a light source that is arranged at the other end of the optical fiber, whereby each exposure is made on a point of the surface which lies opposite the end of the optical fiber, independently of the other points of the surface, and whereby the exposure pattern is selected in advance by means of a control unit.

17. The method according to claim 16, wherein said surface is DNA or PNA and further characterized in that the wavelength of said light is within a range sufficient to cause the deprotecting of nucleotides, nucleotide analogs and peptide nucleic acid and that between said light source and substrate, a plurality of optical fibers is positioned to which light may be selectively coupled to each one and that the surface on which the oligomer synthesis occurs is positioned precisely and rigidly behind said optical fibers and that the surface on which the oligomer synthesis occurs is positioned in a chamber in which the solutions and/or reagents necessary for the DNA or PNA synthesis are contained and are introduced onto the surface by other devices.

18. The method according to claim 16, wherein subsequent to synthesis of DNA or PNA oligomers on the surface hybridization DNA is carried out.

19. The method according to claim 16, further characterized in that a device for the photolithographic exposure of said surface is used for conducting the method, said device comprising at least one light source, a bundle of light-guide optical fibers, and a control unit, wherein each of the optical fibers can be controlled independently of one another by light and/or light can be coupled to each of the optical fibers, independently of one another.

* * * * *